United States Patent [19]
Zeng et al.

[11] Patent Number: 6,008,889
[45] Date of Patent: *Dec. 28, 1999

[54] SPECTROMETER SYSTEM FOR DIAGNOSIS OF SKIN DISEASE

[76] Inventors: Haishan Zeng, 11786 85B Avenue, Delta, BC, Canada, V4C 2W2; Harvey Lui, 3415 West 11th Avenue, Vancouver, BC, Canada, V6R 2K1; Calum MacAulay, 5791 Prince Albert Street, Vancouver, BC, Canada, V5W 3E1; Branko Palcic, 3758 Quesnel Dr., Vancouver, BC, Canada, V6L 2W8; David I. McLean, 1246 West 26th Avenue, Vancouver, BC, Canada, V6H 2A9

[ * ] Notice: This patent issued on a continued prosecution application filed under 37 CFR 1.53(d), and is subject to the twenty year patent term provisions of 35 U.S.C. 154(a)(2).

[21] Appl. No.: 08/843,605

[22] Filed: Apr. 16, 1997

[51] Int. Cl.$^6$ .............................. G01B 9/02; G01N 11/00
[52] U.S. Cl. ........................... 356/73; 356/318; 356/326; 356/445
[58] Field of Search ............................ 356/73, 318, 326, 356/445–448; 128/633, 664, 665; 385/901, 116; 600/473–476

[56] References Cited

U.S. PATENT DOCUMENTS

| | | |
|---|---|---|
| 4,718,417 | 1/1988 | Kittrell et al. . |
| 4,768,513 | 9/1988 | Suzuki .................................... 356/318 |
| 4,927,222 | 5/1990 | Kamiya et al. . |
| 4,957,114 | 9/1990 | Zeng et al. . |
| 5,280,788 | 1/1994 | Janes et al. .............................. 600/476 |
| 5,439,000 | 8/1995 | Gunderson et al. ..................... 600/473 |
| 5,452,723 | 9/1995 | Wu et al. ................................. 356/318 |
| 5,456,260 | 10/1995 | Kollias et al. ........................... 128/665 |
| 5,467,767 | 11/1995 | Alfano et al. . |
| 5,507,287 | 4/1996 | Palcic et al. . |
| 5,522,868 | 6/1996 | Buckley et al. ......................... 128/633 |
| 5,556,612 | 9/1996 | Anderson et al. ....................... 424/59 |
| 5,590,660 | 1/1997 | MacAulay et al. ..................... 600/478 |
| 5,601,087 | 2/1997 | Gunderson et al. .................... 600/473 |
| 5,647,368 | 7/1997 | Zeng et al. . |
| 5,687,730 | 11/1997 | Doiron et al. . |
| 5,701,902 | 12/1997 | Vari et al. . |

OTHER PUBLICATIONS

Zeng, et al., "Optical spectroscopy studies of diseased skin," European BioMedical Optics–BiOS Europe '95, Barcelona, Spain, Sep. 12–16, 1995 (p. 145).

Zeng, et al., "Non–invasive, Bedside Autofluorescence Spectroscopy of Benign and Malignant Skin Lesions," Fourth Meeting of the Western Canadian Society for Clinical and Investigative Dermatology, Jasper, AB, Mar. 24–26, 1995.

Zeng et al, "Quantative Analysis of Laser Induced Autofluorescence Spectra of Diseased Skin," Photonics China '96, Lasers in Medicine and Dentistry: Dignostics and Treatment, Bejing, China, Nov. 4–7, 1996.

(List continued on next page.)

*Primary Examiner*—Robert H. Kim
*Attorney, Agent, or Firm*—Fulwider Patton Lee & Utecht

[57] ABSTRACT

Apparatus for diagnosis of a skin disease site using spectral analysis includes a light source for generating light to illuminate the disease site and a probe unit optically connected to the light source for exposing the disease site to light to generate fluorescence and reflectance light. The probe unit also collects the generated fluorescence and reflectance light and transmits this light to a spectrometer to be analysed. The spectrometer generates and displays spectral measurements of the fluorescence light and the reflectance light which in together assist the user in diagnosing the disease site. The apparatus makes use of a conventional personal computer using a plug-in spectrometer card to provide a compact and low cost system. The system performs combined fluorescence and reflectance spectral analysis in a quick and efficient manner to provide a powerful tool for dermatologic diagnosis.

39 Claims, 11 Drawing Sheets

OTHER PUBLICATIONS

Zeng et al, "Update on Fluorescence Spectroscopy Studies of Diseased Skin," SPIE BiOS '96, San Jose, CA, Jan. 27–Feb. 2, 1996, Paper 2671E–42, Session 8, p. 12.

Lui et al, "Ratio Analysis of Reflectance and Fluorescence Spectra of Diseased Skin," 24$^{th}$ Annual Meeting of the American Society for Photobiology, Atlanta, Georgia, Jun. 15–20, 1996.

Lui et al, "Optical Spectroscopy as a Potential Diagnostic Aid for Dermatology," Clinical Dermatology 2000—An International Congress, Vancouver, BC, May 28–31, 1996, Programme and Abstracts, Abstract 584, p. 176.

Richter, et al., "Photosensitising potency of structural analogues of benzoporphyrin derivative (BPD) in a mouse tumour model," Cancer (1991) 63, 87–93.

Zeng, et al., "Miniature Spectrometer and Multi–Spectral Imager for Skin Diagnoses," Laser in Dermatology, Plastic Surgery and Burn Treatment at Biomedical Optics '95, San Jose, CA, Feb. 4–10, 1995, In: SpiE 2387–09:17, 1995.

Zeng et al., "Update on fluorescence spectroscopy studies of diseased skin," Conference: Lasers in Dermatology and Plastic Surgery, BiOS '96, Jan. 27–Feb. 2, 1996, San Jose, CA.

Zeng et al., "Optical spectroscopy studies of diseased skin—preliminary results," SPIE vol. 2628 / 281–285 (1995).

Zeng et al., "Miniature spectrometer and multi–spectral imager as a potential diagnostic aid in dermatology," SPIE vol. 2387 / 57–61 (1995).

Richter et al., "Preliminary Studies on a More Effective Phototoxic Agent Than Hematophorphyrin," JNCI. vol. 79. No. 6, Dec., 1987, pp. 1327–1332.

Barry BW, et al., "Fourier Transform Raman and Infrared Vibrational Study of Human Skin: Assignment of Spectral Bands", Journal of Raman Spectroscopy, 23:641–645 (1992).

Mahadevan–Jansen A. et al., "Raman Spectroscopy for the Detection of Cancers and Precancers," Journal of Biomedical Optics 1(1), 31–70 (Jan. 1996).

Manoharan R.et al., Histochemical analysis of biological tissues using Raman spectroscopy, Spectrochimica Acta Part A 52:215–249 (1996).

Mizuno A.et al., "Near–Infrared Fourier Transform Raman Spectroscopic Study of Human Brain Tissues and Tumours", Journal of Raman Spectroscopy, 25:25–29 (1994).

Ono I. et al., "Magnetic Resonance Imaging for Diagnosing Skin Tumors", Clinics in Dermatology, 13:393–399 (1995).

Redd D. CB et al., Raman Spectroscopic Charaterization of Human Breast Tissues: Implications for Breast Cancer Diagnosis, Applied Spectroscopy, 47:6: 787–791 (1993).

Zeng, et al., "Novel Microspectrophotometer and its Biomedical Applications", Optical Engineering, SPIE vol. 32: No. 8, 1809–1814 (1993).

Zeng, et al., "Laser–induced changes in autofluorescence of in vivo skin", Laser–Tissue Interaction IV, SPIE vol. 1882:278–290 (1993).

Bissonnette R.et al., "Detection of Autofluorescence Due to Protoporphyrin IX in the Stratum Corneum of Psoriasis Plaques," 25$^{th}$ Annual Meeting of the American Society for Photobiology, St. Louis, Missouri, Jul. 5–10, 1997.

Zeng, et al., "Reconstruction of in vivo skin autofluorescence spectrum from microscopic properties by Monte Carlo simulation", Journal of Photochemistry and Photobiology B: Biology, 234–240 (1996).

Zeng, et al., "Spectroscopic and Microscopic Characteristics of Human Skin Autofluorescence Emission", Photochemistry and Photobiology, 61:639–645, 1995.

Tanaka K. et al., "Compound parabolic concentrator probe for efficient light collection in spectroscopy of biological tissue", Applied Optics, 35(4):758–763 (1996).

Williams AC et al., "A Critical Comparison of Some Raman Spectroscopic Techniques for Studies of Human Stratum Corneum", Pharmaceutical Research, 10 (11): 1642–1647 (1993).

Williams AC et al., "Comparison of Fourier Transform Raman Spectra of Mammalian and Reptilian Skin", Analyst, vol. 119:563–566 (1994).

Zeng H et al., "A computerized autofluorescence and diffuse reflectance spectroanalyser system for in vivo skin studies", Phys. Med. Biol. vol. 38:231–240 (1993).

Zeng H et al., Monte Carlo modeling of tissue autofluorescence measurement and imaging, from Proceedings of Advances in Laser and Light Spectroscopy to Diagnose Cancer and Other Diseases; SPIE vol. 2135:94–104 (1994).

SPECTROMETER SYSTEM FOR DIAGNOSIS OF SKIN DISEASE

FIELD OF THE INVENTION

This invention relates to an apparatus for assisting in diagnosis of skin disease by making spectral measurements of fluorescence and reflectance light from the skin disease site.

BACKGROUND OF THE INVENTION

Currently, clinical diagnosis of skin disease is generally accomplished by visual inspection under white light illumination. In this process, the reflectance light of a skin lesion is examined. Visual diagnosis alone may not be particularly accurate for early detection of skin cancer since many skin conditions have a similar appearance under white light. Therefore, when a suspect lesion is identified by visual examination, a biopsy is often performed for a definitive diagnosis. Not only is it crucial to diagnose skin pre-cancer or skin cancer at an early stage when it is curable, but it is also important to improve the clinical diagnosis of suspected skin lesions so as to avoid unnecessary skin biopsies.

Several approaches have been tried to improve dermatologic diagnosis. Digital processing of reflectance images has been extensively investigated recently. Although reflectance imaging has led to improvements in the registration, recording, and documentation of skin lesions, there has been little improvement in the diagnostic accuracy. The foregoing approach does not provide any additional data to the physician making the visual assessment because it is still based on the reflectance pattern of a lesion under white light illumination which is essentially the same pattern a human observer sees.

An alternative approach is ultraviolet (UV) or infrared (IR) photography which does extend visual perception of a physician to the UV or IR reflectance patterns. However, the inconvenience due to delays in processing of film images renders this technique impractical for everyday use.

A further alternative approach that is already in widespread medical use involves a "Wood's lamp" which consists of a mercury discharge lamp associated with a filter that transmits UVA light with a 365 nanometer peak while absorbing visible light. When this device is used to assist in skin diagnosis, the eye serves as both the detector and the long pass filter. The eye is not sensitive to UV light, but is sensitive to visible fluorescence light when the "Wood's lamp" is used in a darkened room, where the physician sees an image of a fluorescing disease site. The "Wood's lamp" is useful for the diagnosis of some skin conditions such as tinea capitis, tinea versicolor, erythrasma, and some pseudomonas infections, as well as aiding in the detection and diagnosis of hypopigmented skin. It is of no value in conditions where the fluorescence is not in the visible spectrum.

SUMMARY OF THE INVENTION

The apparatus and method of the present invention use spectral measurements of both fluorescence light and reflectance light from a disease site to aid in the medical assessment of skin conditions and the diagnosis of cutaneous diseases.

Accordingly, the apparatus of the present invention provides apparatus for diagnosis of a skin disease site using spectral analysis comprising:

a light source for generating light to illuminate the disease site;

a probe means to conduct the illumination light from the light source to the disease site and to collect the reflected and fluorescence light and conduct said light to be analysed; and spectral analysis means optically connected to the probe means for generating and displaying spectral measurements of the fluorescence light and the reflectance light to assist the user in diagnosing the disease site.

In a further aspect, the present invention provides a method for diagnosis of a skin disease site using spectral analysis comprising the steps of:

illuminating the disease site with a light source to generate fluorescence and reflectance light at the disease site;

collecting the generated fluorescence and reflectance light;

conducting a spectral analysis of the collected light using a spectrometer;

displaying spectral measurements of the fluorescence light and the reflectance light; and analysing the measured fluorescence and reflectance spectra together to make a diagnosis of the disease site.

In a preferred embodiment, the apparatus of the present invention includes a compact spectrometer connected to a personal computer, a fluorescence excitation light source with a shutter, a white light source with a shutter, a bifurcated fibre bundle, a light coupler, a skin probe, and controlling electronics. The system is designed to automatically switch between the fluorescence excitation light and the white light sources and complete fluorescence and reflectance spectral measurements of a skin disease site sequentially in a few seconds. The system exploits the spectral differences of different skin diseases to aid in the dermatologic diagnosis. In particular, the apparatus provides a low cost, compact system that is capable of quickly and efficiently performing combined fluorescence and reflectance spectral analysis.

BRIEF DESCRIPTION OF THE DRAWINGS

Aspects of the present invention are illustrated, merely by way of example, in the accompanying drawings in which.

DESCRIPTION OF THE PREFERRED EMBODIMENTS

Figure 1:
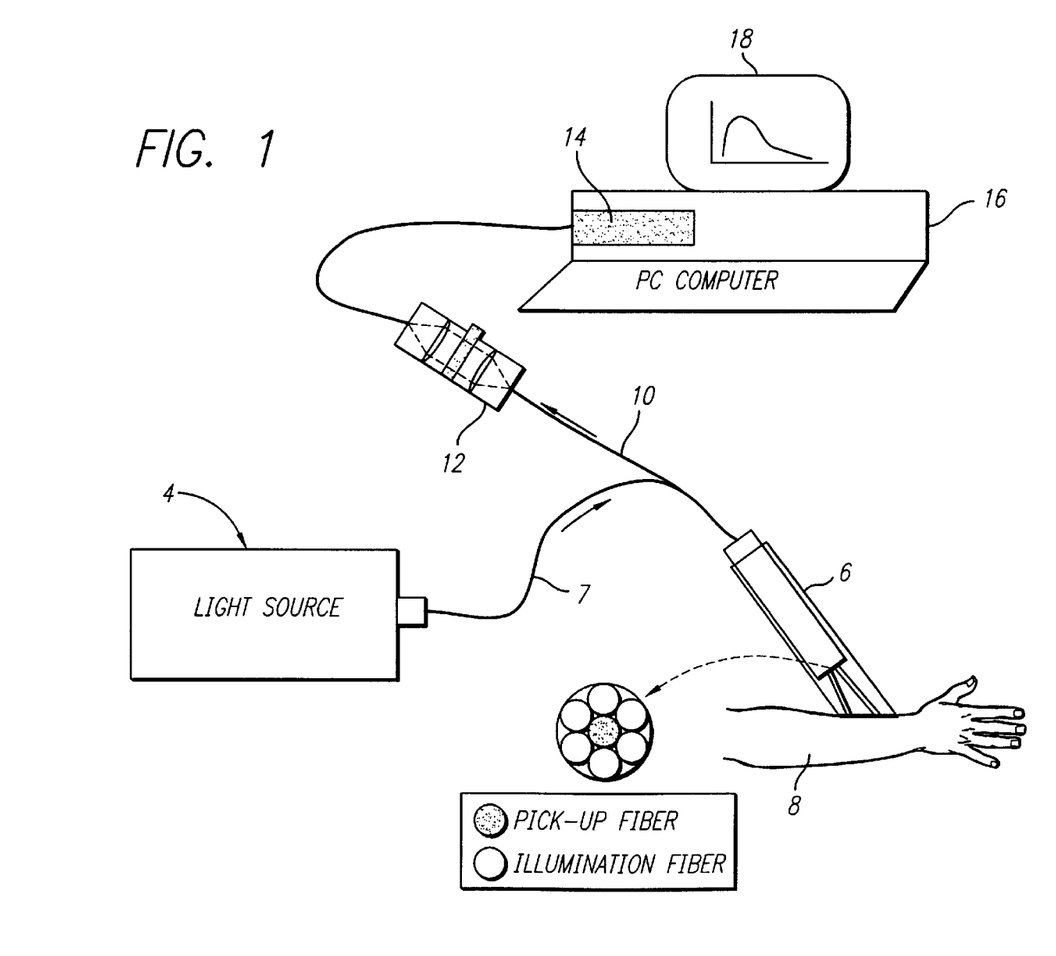
FIG. 1 is a schematic diagram showing an embodiment of the apparatus of the present invention.

Referring to FIG. 1, there is a schematic view of the apparatus of the present invention for diagnosing skin diseases. In essence, the apparatus includes a light source 4 and a probe 6 optically connected via optical fibre 7 to light source 4 for exposing a skin disease site 8 to light. The light from source 4 generates fluorescence and reflectance light at disease site 8 that is collected by probe 6 and transmitted by optical fibre 10 via light filter 12 to spectral analysis means in the form of a spectrometer 14. Spectrometer 14 generates and displays spectral measurements of the fluorescence and reflectance light on the monitor 18 of a computer 16 for viewing by a user to assist in the diagnosis of the disease site.

Figure 2:
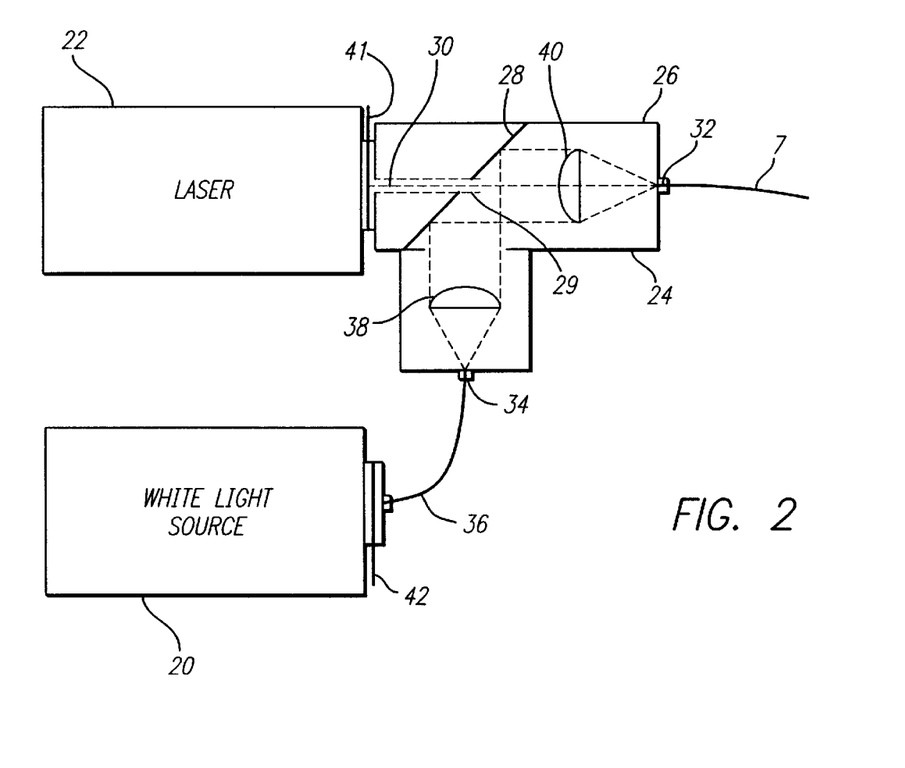
FIG. 2 is a detail view of light coupler arrangement of the present invention that connects a white light source and a laser light source.

In a preferred embodiment of the present invention, the fluorescence and reflectance light is acquired and analysed sequentially. In order to accomplish this, light source 4 preferably comprises a white light source 20 for reflectance measurements and an excitation light source 22 for fluorescence measurements as best shown in FIG. 2. Excitation light source 22 can be a Helium-Cadmium (442 nm) laser and white light source 20 can be a quartz tungsten halogen lamp.

The two light sources 20 and 22 are joined together by an optical coupler 24 that allows light from either source to be transmitted via the same optical fibre bundle 7. Optical coupler 24 comprises a sealed enclosure 26 housing an angled reflecting surface or mirror 28 having a small aperture 29. A laser light port 30 is formed in enclosure 26 to admit laser light from laser light source 22. Port 30 is aligned with aperture 29 to permit passage of laser light directly through mirror 28 to a light exit port 32 which is connectable to optical fibre bundle 7 and probe unit 6. A white light port 34 is formed in enclosure 26 and positioned with respect to mirror 28 such that white light is reflected through an angle to be incident upon light exit port 32. White light port 34 is optically connectable to white light source 20 via a short length of optical fibre 36. Lenses 38 and 40 are also provided within enclosure 26 to collimate white light from port 34 onto the mirror surface and to focus reflected light from the mirror onto light exit port 32.

Associated with each light source are shutter systems 41 and 42 to permit switching between excitation laser light source 22 and white light source 20, respectively, such that the disease site is illuminated sequentially by only one of the light sources at a time. Shutter systems 41 and 42 are preferably electronic and controlled by computer 16 (FIG. 1). Computer 16 is programmed to close shutter 41 while shutter 42 is open to obtain reflectance light measurements of the disease site and vice versa to obtain fluorescence light measurements.

Figure 3:
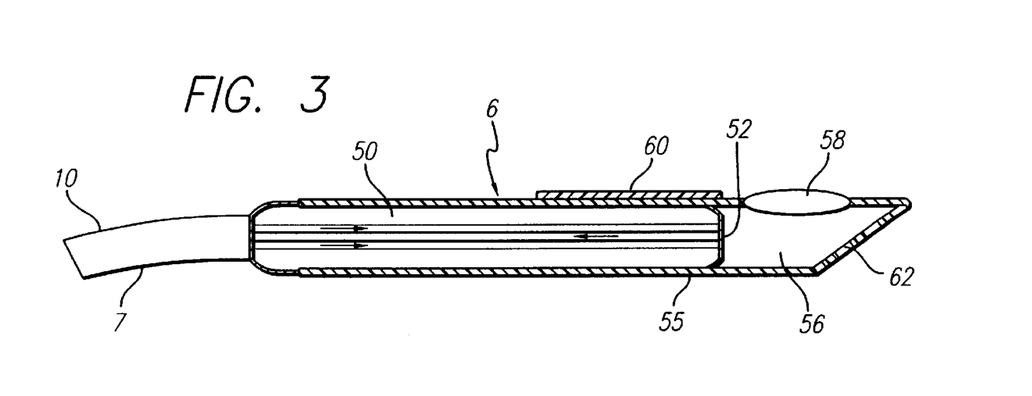
FIG. 3 is a detail section view of the probe member according to a preferred embodiment of the present invention.
Figure 4A:
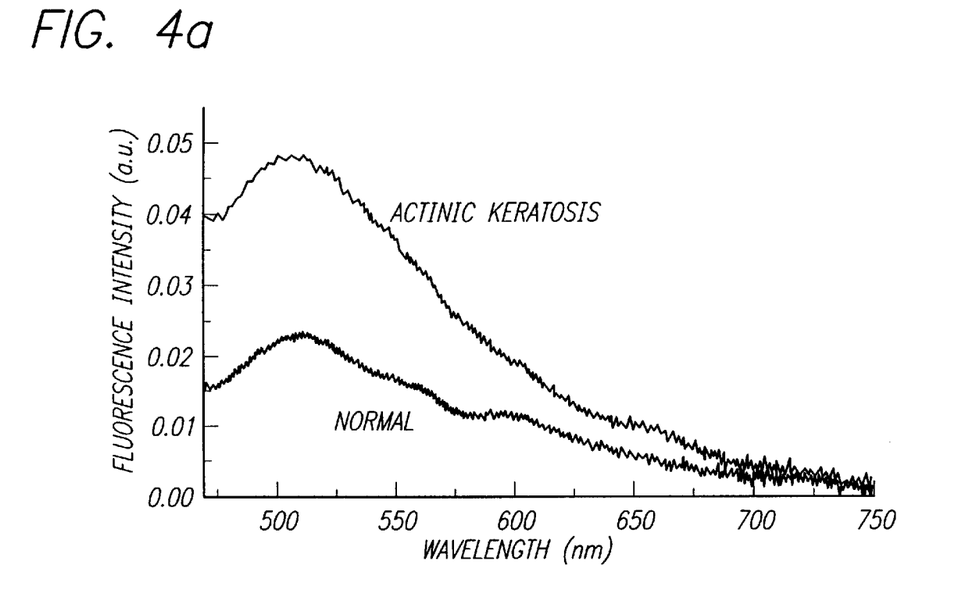
FIG. 4a to 4h are fluorescence and reflectance spectral measurements of various skin diseases that illustrate how viewing both spectral measurements together assists a user in identifying a particular skin disease.
Figure 4B:
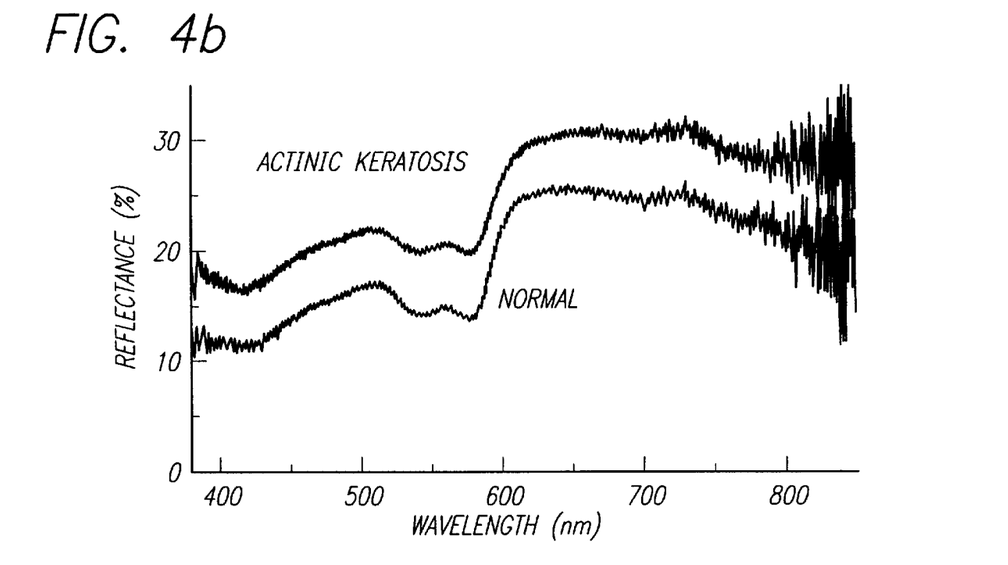
Figure 4C:
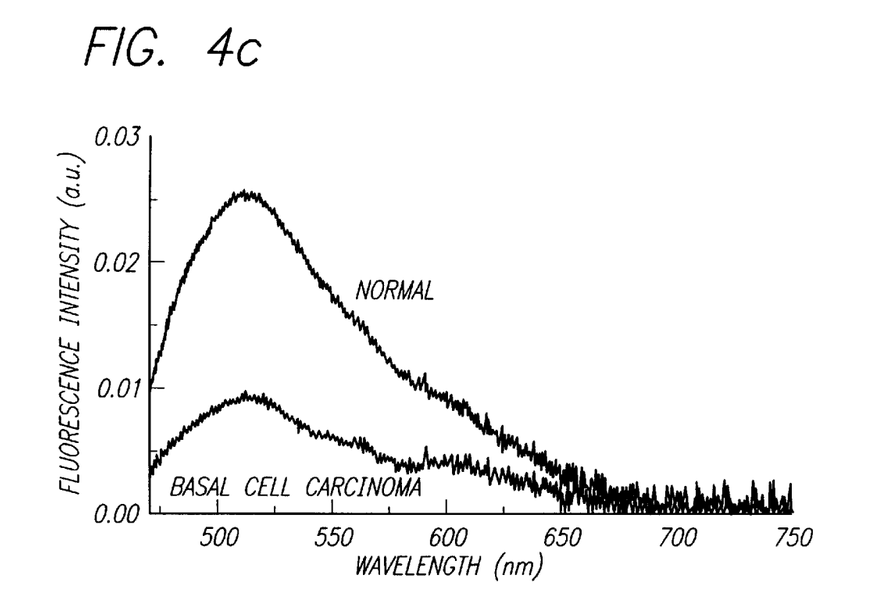
Figure 4D:
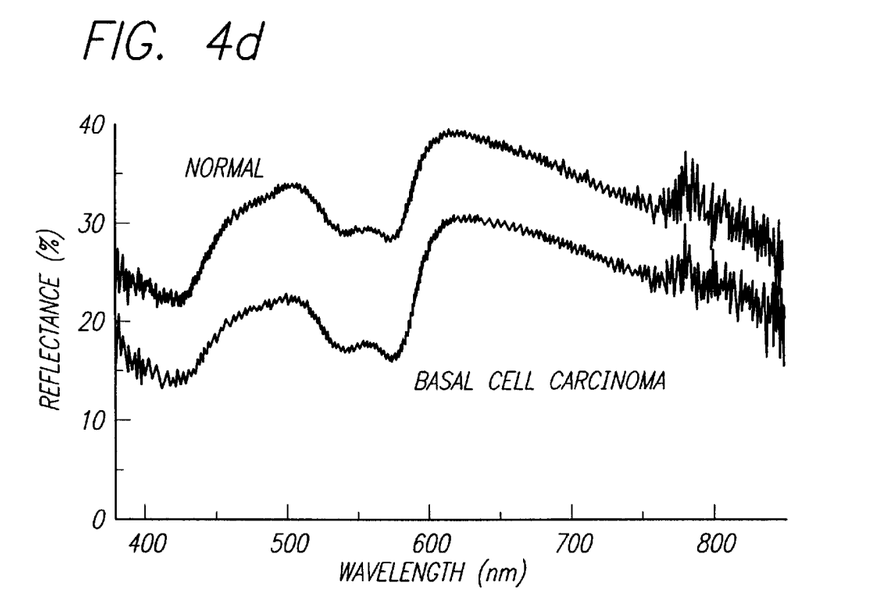
Figure 4E:
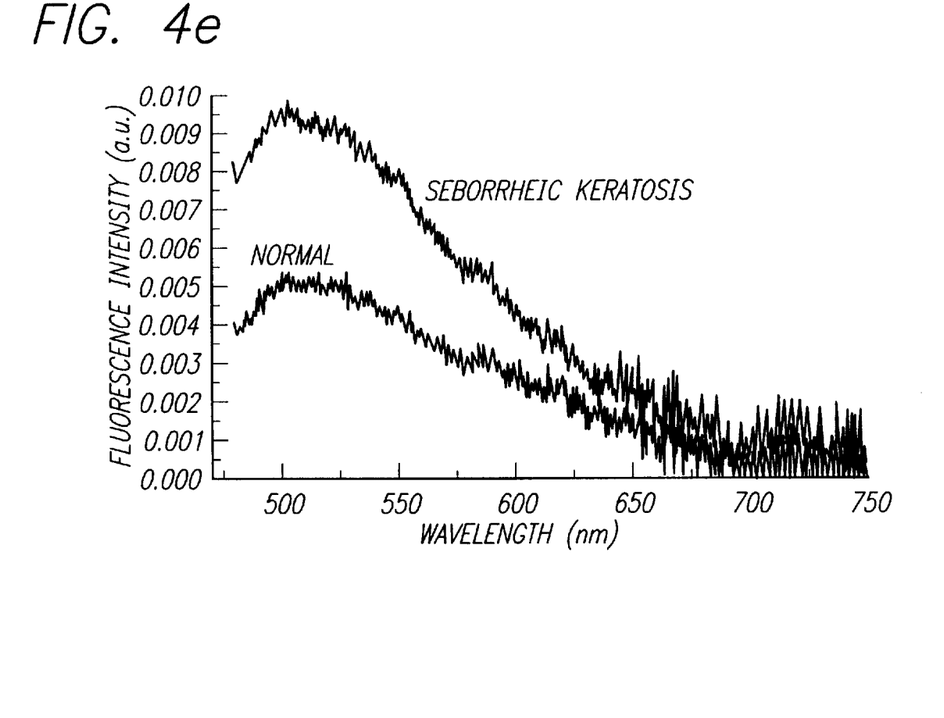
Figure 4F:
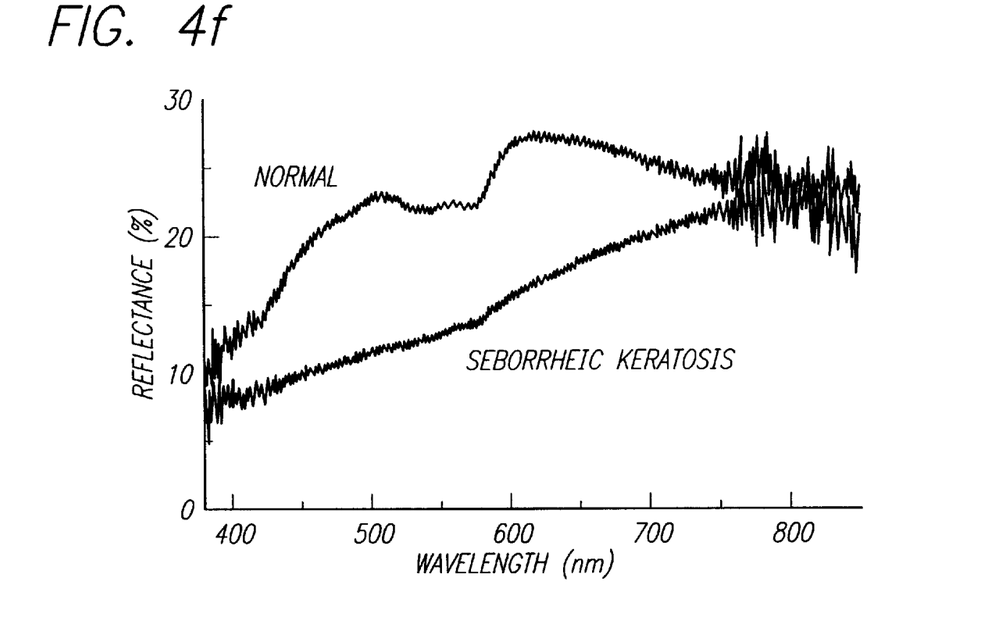
Figure 4G:
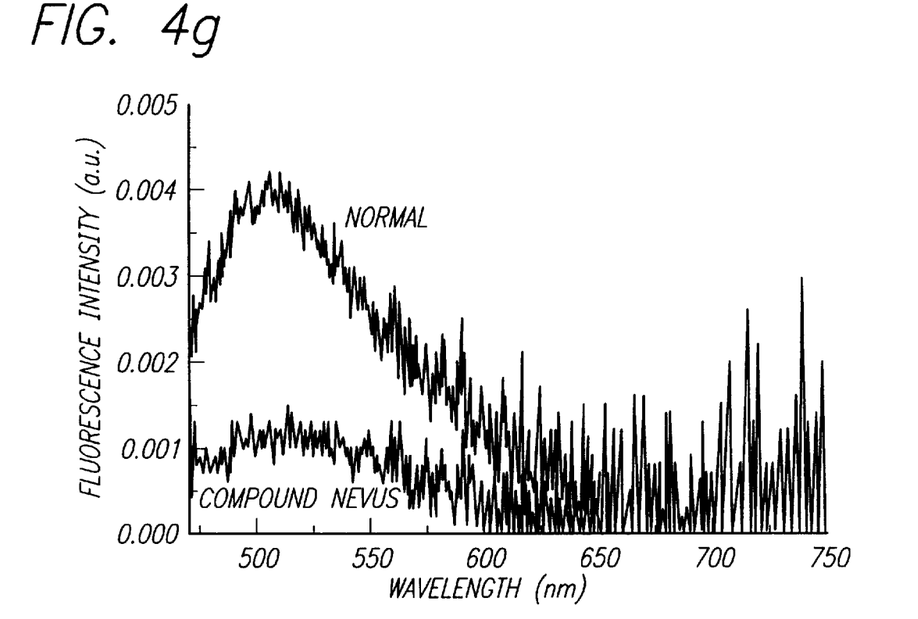
Figure 4H:
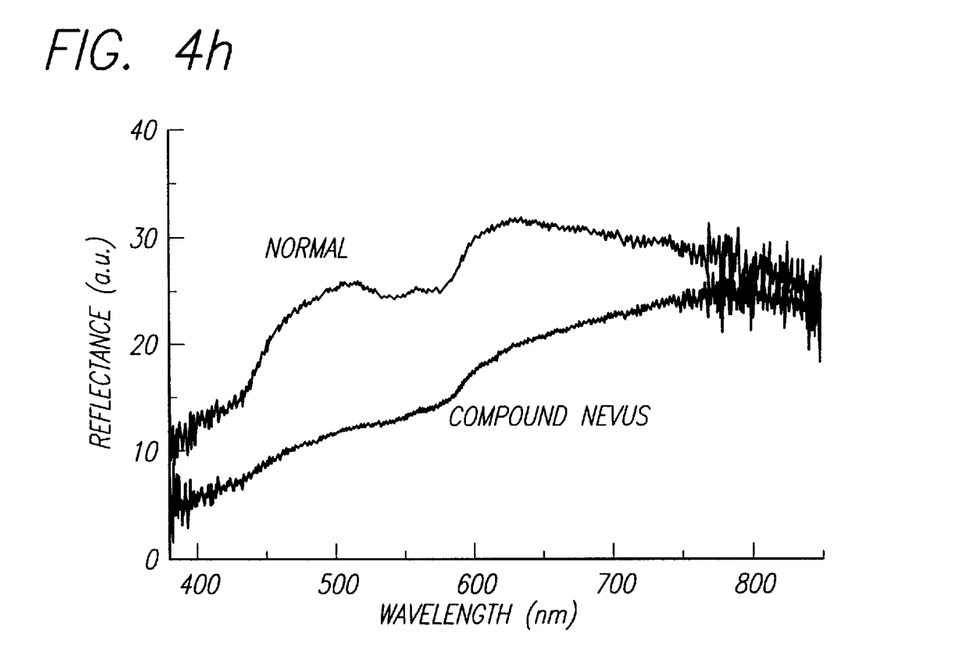

FIG. 3 is a detailed view of the probe unit 6 used to illuminate disease site 8 with light from the light sources and collect fluorescence and reflectance light from the site to transmit to spectrometer 14. Probe unit 6 comprises a generally cylindrical member 50 housing combined optical fibre bundles 7 and 10 that extend to a distal end 52 of the cylindrical member. An opaque sleeve member 55 is telescopically mounted on cylindrical member 50 for slidable movement. The overlap of sleeve member 55 with distal end 52 of cylindrical member 50 defines a chamber 56 that is positionable over skin disease site 8 of interest. Fibre bundles 7 communicate with chamber 56 to transmit illumination light into the chamber and fibre bundle 10 communicates with the chamber to transmit fluorescence or reflectance light from the chamber to the spectrometer 14. Slidable movement of sleeve member 55 with respect to cylindrical member 50 adjusts the length of chamber 56 and hence the distance between the fibre bundles at distal end 52 to vary the size of the illumination spot at disease site 8. By adjusting the length of chamber 56, different sizes and areas of disease sites can be examined and diagnosed.

Free end 62 of sleeve member 56 is preferably cut at a 45 degree angle to the longitudinal axis of the sleeve. This avoids the collection of specular reflected light from the skin surface. In addition, sleeve member 55 is preferably formed with a window 58 to allow observation inside the chamber when positioned over a disease site to ensure proper positioning. There is a slidable cover 60 to seal the window when the apparatus is in use. The design of probe unit 6 is such that the apparatus of the present invention can be used in a normally lighted room since no ambient light is able to enter chamber 56 and interfere with spectral measurement when chamber 56 is positioned over a disease site and cover 60 is closed over window 58.

The small cross-sectional area of sleeve member 55 is all that actually contacts the skin at disease site 8 in order to minimise the pressure on the disease site. Any excessive pressure on the skin at the disease site will affect the blood content in the skin tissue at the disease site which will affect the resulting spectral measurements.

Fluorescence light and reflectance light from the disease site is transmitted via optical fibre 10 to spectrometer 14. When shutter 41 is open to transmit excitation laser light to the disease site, filter 12 is used to pass fluorescence light to the spectrometer and block any reflected excitation light. For example, if a He-Cd laser is used to generate an excitation light of 442 nm wavelength, a 470 nm long pass filter 12 will pass fluorescence light with wavelengths larger than 470 nm but will block reflected excitation light.

Preferably, spectrometer 14 is a computer interface card installable in an interface slot of computer 16 which is preferably a standard personal computer (PC) having an I/O bus appropriate to receive the interface card. Such a PC based plug-in spectrometer is available from Ocean Optics, Inc. (Dunedin, Fla.) under the name Model PC 1000. The plug-in spectrometer is adapted to connect to optic fibre 10 and includes a miniature monochromalor, a CCD linear array detector, and all data acquisition and controlling electronics on the interface card. A spectrometer version for laptop computers using a PCMCIA port may also be used.

As previously described, computer 16 controls shutter systems 41 and 42. Computer 16 also controls spectrometer 14 in order to acquire spectral measurements of the fluorescence and reflectance light from the disease site. In prototype testing, the necessary spectral measurements of fluorescence and reflectance light were accomplished in a few seconds.

FIGS. 4a to 4h illustrate typical fluorescence and reflectance spectra of particular skin diseases acquired using the apparatus and method of the present invention. Using reflectance spectra alone or visual inspection of white light illumination, it can be difficult to differentiate between various skin conditions such as seborrheic keratosis (FIG.

4f) and compound nevus (FIG. 4h), or between actinic keratosis (FIG. 4b) and basal cell carcinoma (FIG. 4d) since each pair of skin diseases have similar reflectance spectra. However, when a user also considers the corresponding fluorescence spectrum for the particular skin disease, it is possible to differentiate between seborrheic keratosis (FIG. 4e) with a fluorescence intensity higher than normal skin and compound nevus (FIG. 4g) with a fluorescence intensity much lower than normal skin. In a similar manner, it is possible to use fluorescence spectra to differentiate between actinic keratosis (FIG. 4a) with a fluorescence intensity higher than normal skin and basal cell carcinoma (FIG. 4c) having a fluorescence intensity lower than normal skin.

It is important to note that the apparatus and method of the present invention rely on using both reflectance and fluorescence spectral measurements in combination to assist in diagnosis. In general, comparing only one type of spectral measurements results in difficulties in distinguishing between certain skin diseases. For example, using only fluorescence spectra for each skin disease makes it difficult to distinguish between actinic keratosis (FIG. 4a) and seborrheic keratosis (FIG. 4e) or between basal cell carcinoma (FIG. 4c) and compound nevus (FIG. 4g) as each of these particular pairs of skin diseases have similar fluorescence spectra. The fact that the above pairs of skin diseases have different reflectance spectra allow them to be distinguished clearly from each other.

By way of a simplified example, the following chart shows the manner in which the fluorescence spectrum and the reflectance spectrum can be analysed to distinguish between the various skin diseases.

TABLE 1

Distinguishing between skin conditions by considering Fluorescence and Reflectance Spectral Characteristics

| Fluorescence | | |
|---|---|---|
| Intensity Higher than Normal | Actinic Keratosis | Seborrheic Keratosis |
| Intensity Lower than Normal | Basal Cell Carcinoma | Compound Nevus |
| | Reflectance Curve Slope Similar to Normal | Reflectance Curve Slope Larger than Normal |

Reflectance

Figure 5:
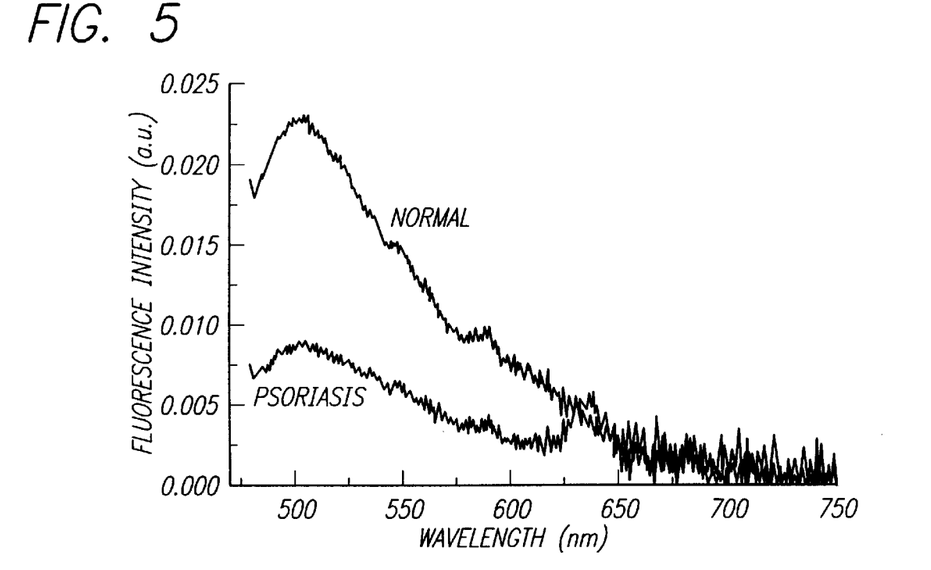
FIG. 5 is a fluorescence spectrum of a psoriasis lesion.
Figure 6:
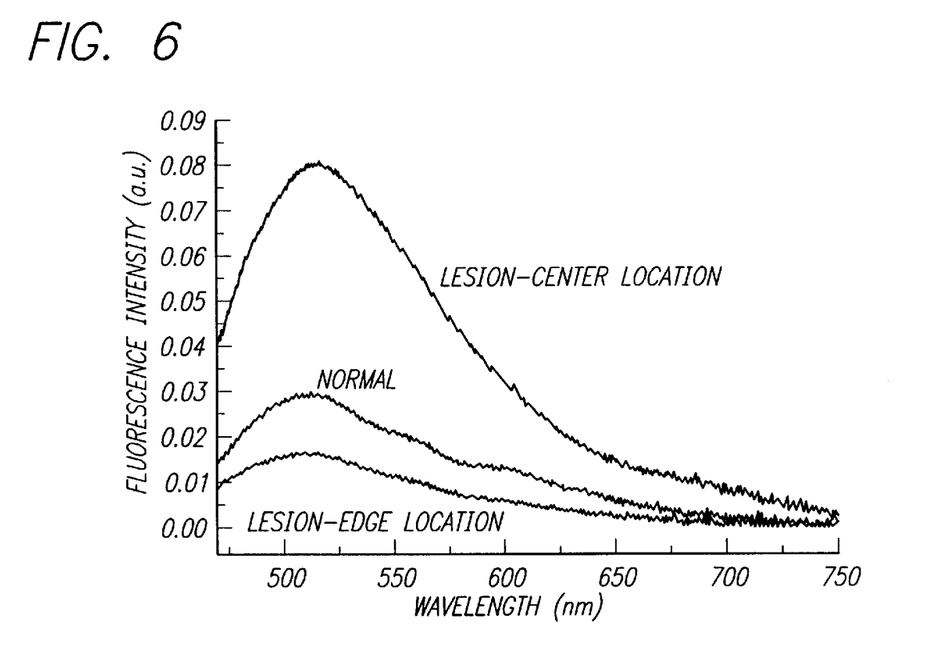
FIG. 6 is a fluorescence spectrum of a squamous cell carcinoma (SCC)

More sample spectra are shown in FIGS. 5–8. FIG. 5 is the fluorescence spectrum of a psoriasis lesion, showing a unique spectral peak at around 635 nm, allowing psoriasis to be easily differentiated from other skin lesions. FIG. 6 shows fluorescence spectra of a squamous cell carcinoma (SCC). The fluorescence intensity over a SCC lesion is not uniformly distributed. As shown, in some places within the lesion, the fluorescence intensity is higher than normal skin, while in other locations, the fluorescence intensity is lower than normal. This feature for SCC lesions is different from that of basal cell carcinomas (BCC), where the fluorescence intensity is uniformly lower than found in surrounding normal skin.

It is important to compare lesional spectra to the spectra of the surrounding normal skin in order to assess the spectral features of diseased skin. This comparison compensates for the regional variations in skin optical properties and spectral features. It also adjusts for intersubject variability.

To further standardise the method of the present invention, we have developed a ratio technique to aid spectra interpretation. In the ratio analysis technique, lesional spectra (reflectance or fluorescence) are divided by the corresponding spectra of the surrounding normal skin. In this way, the relative spectral intensity changes are quantified, and the spectral shape changes are enhanced and more easily visualised on the spectral curves.

Figure 7A:
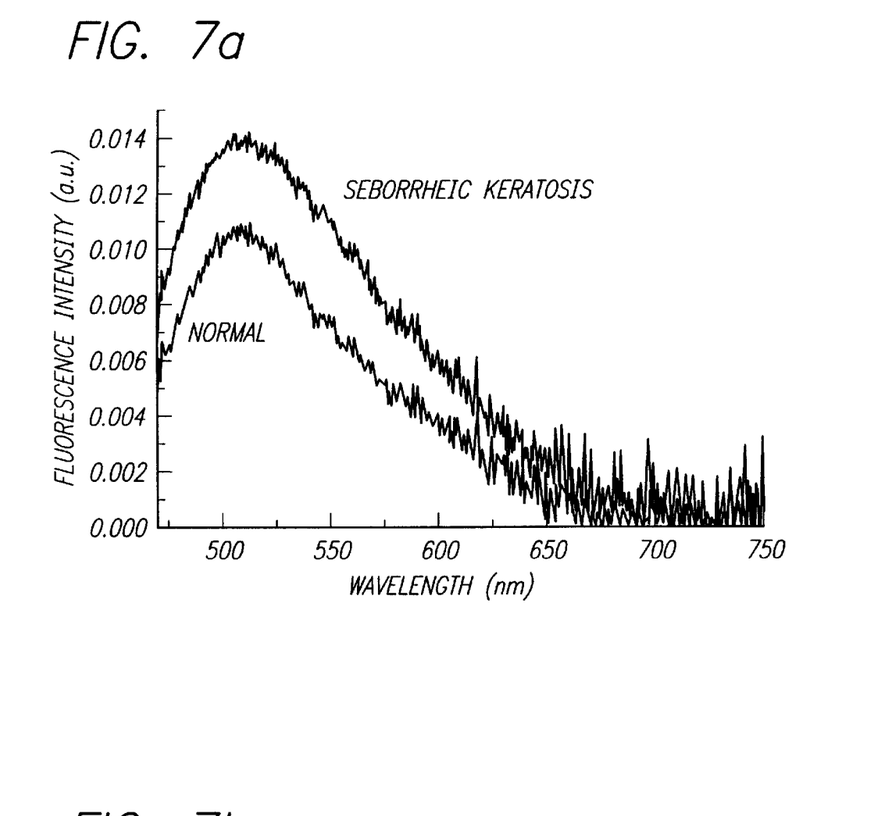
FIG. 7a shows the fluorescence spectra of normal skin and seborrheic keratosis.
Figure 7B:
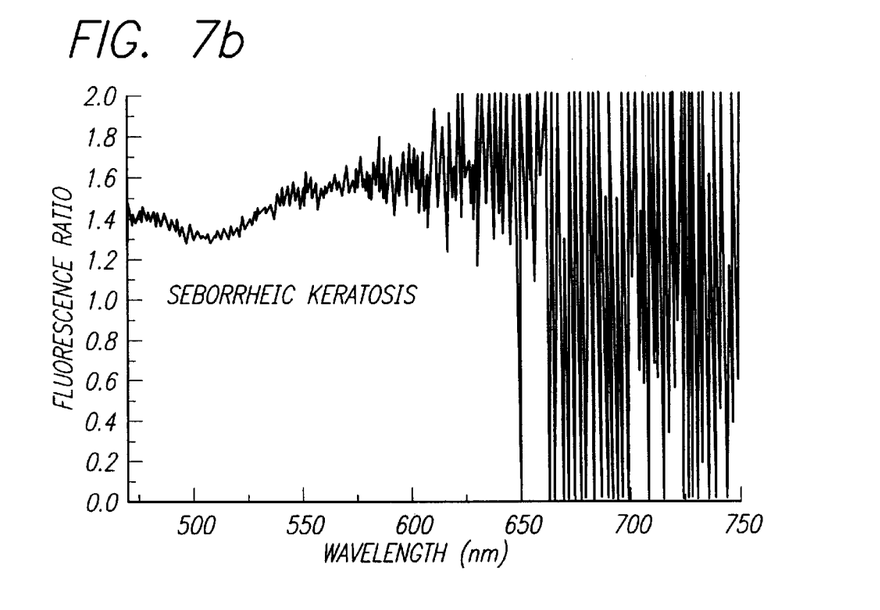
FIG. 7b shows the fluorescence ratio spectrum equal to the seborrheic keratosis fluorescence spectrum divided by the normal skin fluorescence spectrum.

FIGS. 7a to 7d show the original spectra and the ratio spectra of a seborrheic keratosis. FIG. 7a is the original fluorescence spectra, the lesion has higher fluorescence intensity than the normal, but the shape of the two curves are visually about the same. FIG. 7b is the fluorescence ratio spectrum which equals the lesion fluorescence spectrum divided by the normal fluorescence spectrum. The absolute value of the ratio spectrum is larger than 1, indicating that the lesion has higher fluorescence intensity than the normal and it indicates quantitatively how many times higher is the lesion signal than the normal at each wavelengths. Interestingly, a valley around 510 nm is shown on the ratio spectrum curve, which is unique to seborrheic keratosis and which cannot be discerned by only looking at the original spectra shown in FIG. 7a. Therefore, using the ratio technique, new spectral features have been revealed from the original spectra and new diagnostic information has been obtained.

Figure 7C:
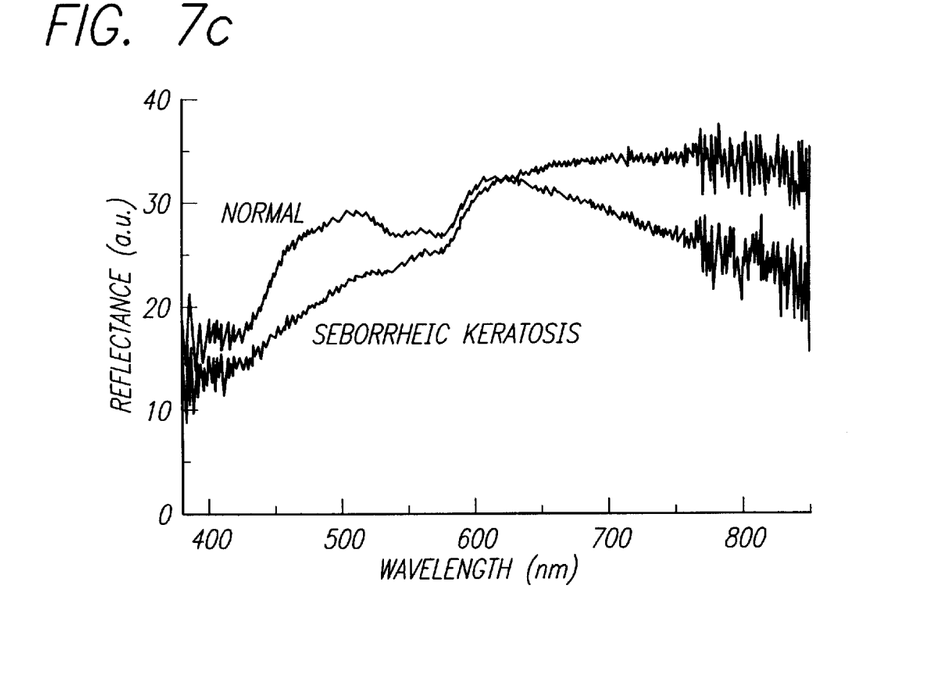
FIGS. 7c and 7d show the reflectance spectra and reflectance ratio spectrum, respectively, of seborrheic keratosis and normal skin.
Figure 7D:
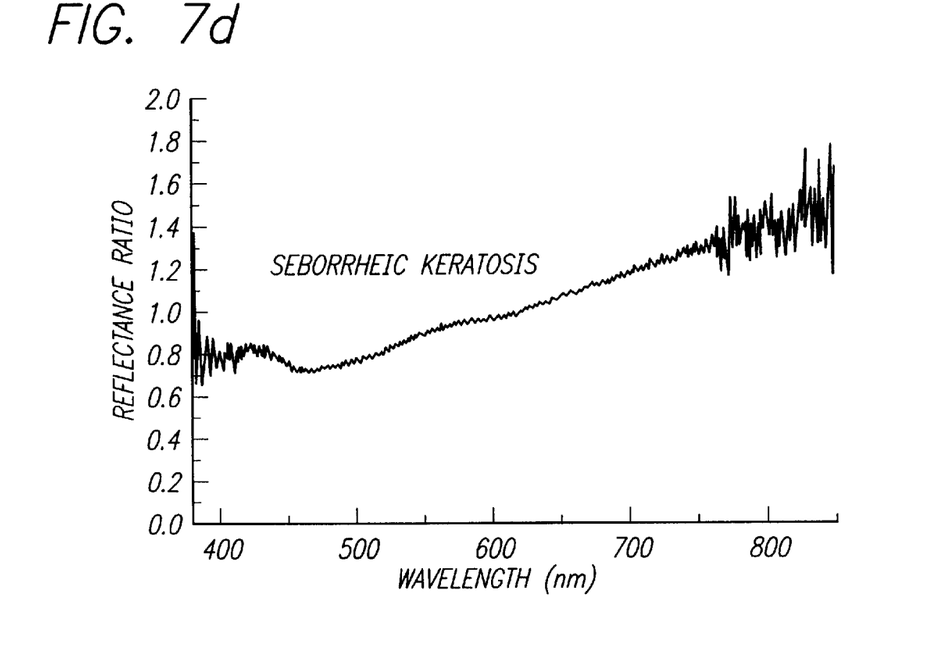

FIG. 7c is the reflectance spectra of the same seborrheic keratosis lesion and its surrounding normal skin. FIG. 7d is the reflectance ratio spectrum which equals the lesion reflectance spectrum divided by the normal reflectance spectrum. The reflectance ratio spectrum of seborrheic keratosis shows lower values at short wavelengths and higher values at longer wavelengths and is a quantitative representation of the slope changes described in table 1.

Figure 8A:
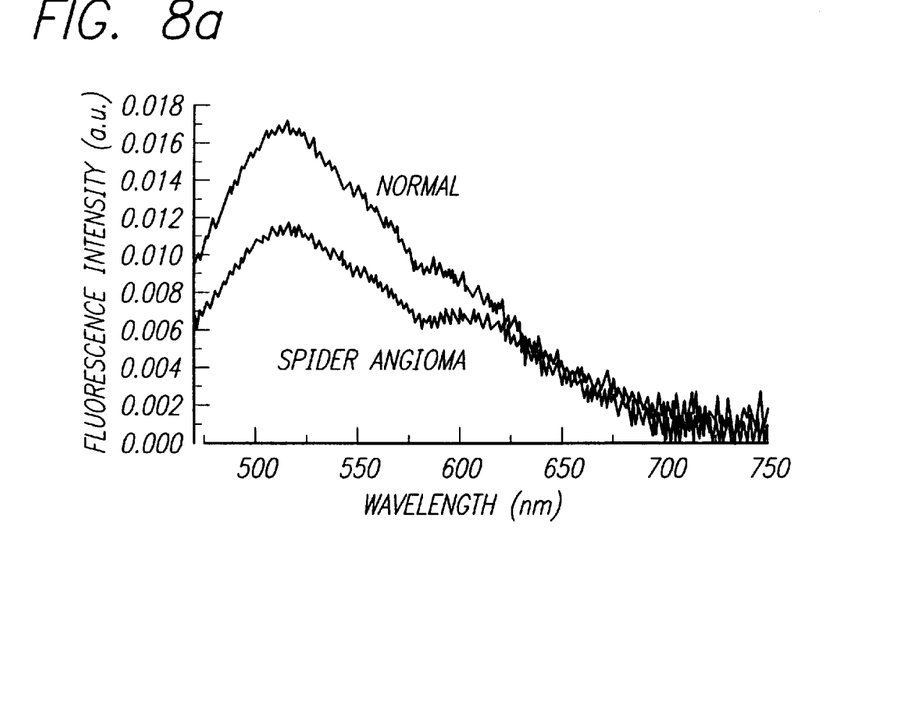
FIG. 8a shows the fluorescence spectra of spider angioma and normal skin.
Figure 8B:
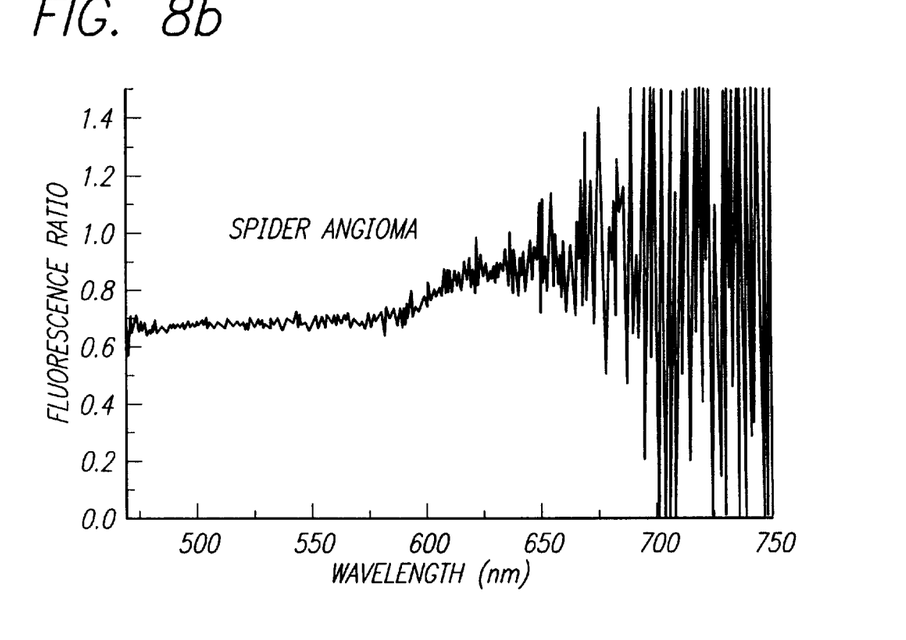
FIG. 8b shows the fluorescence ratio spectrum equal to the angioma fluorescence spectrum divided by the normal skin fluorescence spectrum.
Figure 8C:
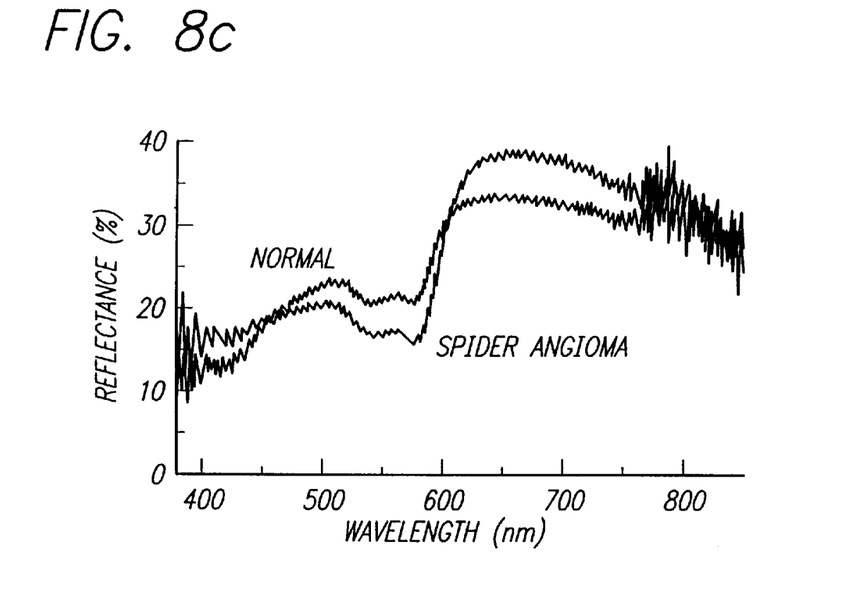
FIGS. 8c and 8d show the reflectance spectra and reflectance ratio spectrum, respectively, of spider angioma and normal skin.
Figure 8D:
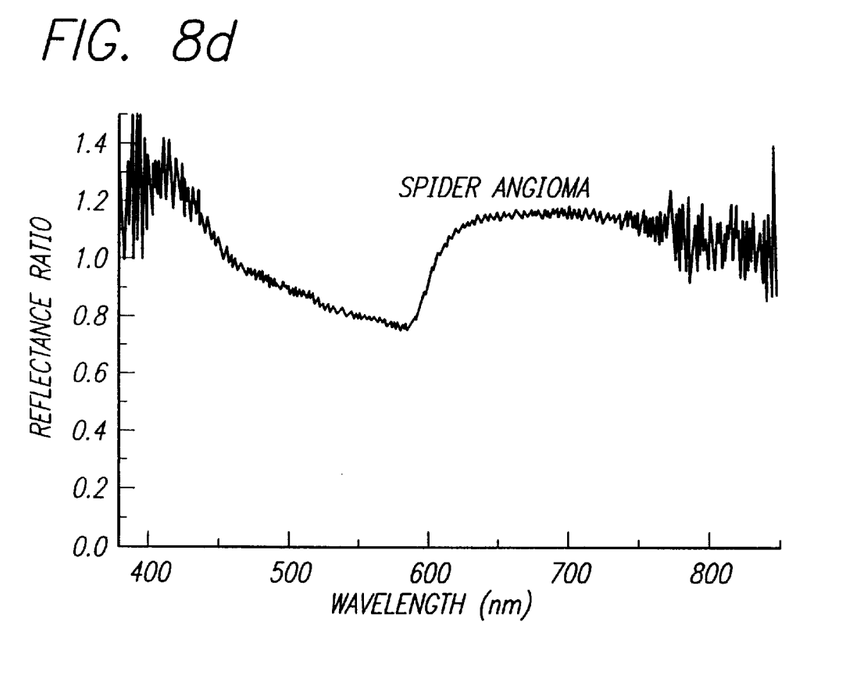

FIG. 8a is the fluorescence spectra of a spider angioma and its surrounding normal skin. The lesion has lower fluorescence intensity than normal skin. FIG. 8b is the fluorescence ratio spectrum of the same lesion. The ratios with values less than 1 indicate that the lesional fluorescence intensity is lower than its surrounding normal skin while the numerical ratio values quantify this difference as a function of wavelength. FIG. 8c shows the reflectance spectra of the same spider angioma, and FIG. 8d the reflectance ratio spectrum. The reflectance ratio spectra of spider angiomas have a unique "saw-tooth" shape with a minimum at around 600 nm. This unique spectral feature can be used to easily differentiate spider angioma from other skin lesions.

Although the present invention has been described in some detail by way of example for purposes of clarity and understanding, it will be apparent that certain changes and modifications may be practised within the scope of the appended claims.

We claim:

1. Apparatus able to diagnose a disease selected from the group consisting of actinic keratosis, seborrheic keratosis, basal cell carcinoma and compound nevus at a skin disease site using spectral analysis comprising:

a light source for generating light to illuminate the disease site;

a probe means optically connected to the light source to expose the disease site to light to generate fluorescence and reflectance light and collect said generated fluorescence and reflectance light;

spectral analysis means optically connected to the probe means for generating spectral measurements of the fluorescence light and the reflectance light to assist the user in diagnosing the disease site;

a plurality of comparison spectra corresponding to, and able to distinguish between, each of actinic keratosis, seborrheic keratosis, basal cell carcinoma and compound nevus wherein the spectra indicate that if the reflectance curve slope is similar to normal and the fluorescence intensity is higher than normal, then the disease is actinic keratosis; if the reflectance curve slope is similar to normal and the fluorescence intensity is lower than normal, then the disease is basal cell carcinoma; if the reflectance curve slope is larger than normal and the fluorescence intensity is higher than normal, then the disease is seborrheic keratosis; and, if the reflectance curve slope is larger than normal and the fluorescence intensity is lower than normal, then the disease is compound nevus; and a display indicating the presence or absence at the skin disease site of actinic keratosis, seborrheic keratosis, basal cell carcinoma or compound nevus.

2. Apparatus as claimed in claim 1 in which the light source comprises an excitation light source and a white light source.

3. Apparatus as claimed in claim 2 in which the excitation light source is a Helium-Cadmium laser and the white light source is a quartz tungsten halogen lamp.

4. Apparatus as claimed in claim 2 including a shutter system to switch between the excitation light source and the white light source such that the disease site is illuminated sequentially by one of the light sources at a time.

5. Apparatus as claimed in claim 4 including computer control means to control the shutter system by switching between light sources and to control the spectral analysis means in order to acquire spectral measurements of the fluorescence and reflectance light.

6. Apparatus as claimed in claim 5 in which the computer control means comprises a personal computer and the spectral analysis means comprises a computer interface card installable in an interface slot of the computer to function as a spectrometer.

7. Apparatus as claimed in claim 6 in which the spectrometer computer interface card includes a miniature monochromator, a CCD linear array detector, means for optically connecting to the probe means, and data acquisition and controlling circuitry.

8. Apparatus as claimed in claim 2 including a light filter selected to pass fluorescence light and block reflected excitation light.

9. Apparatus as claimed in claim 2 in which the light source is optically connected to the probe means and the probe means is optically connected to the spectral analysis means by optical fibre bundles.

10. Apparatus as claimed in claim 9 including an optical coupler for connecting the white light source and the excitation light source to deliver light via the same optical fibre bundle.

11. Apparatus as claimed in claim 10 in which the optical coupler comprises:

an enclosure housing, an angled reflecting surface having an aperture;

a laser light port in the enclosure aligned with the aperture to permit passage of laser light directly through the angled reflecting surface, the laser light port being optically connectable to a laser light source;

a light exit port from the enclosure aligned with the laser light port and the aperture through the angled reflecting surface, the light exit port being optically connectable to the probe means; and a white light port in the enclosure positioned with respect to the angled reflecting surface such that white light is reflected through an angle to be incident upon the light exit port, the white light opening being optically connectable to the white light source.

12. Apparatus as claimed in claim 9 in which the probe means comprises an elongate member having an open end defining a chamber with opaque walls that is positionable over the disease site to exclude external light from the chamber, the chamber being connected to the optical fibre bundles for receiving light from the light sources and transmitting fluorescence light and reflectance light to the spectral analysis means.

13. Apparatus as claimed in claim 12 in which the elongate member comprises:

a generally cylindrical member housing the optical fibre bundles that extend to a distal end of the cylindrical member;

a sleeve member that telescopes over the generally cylindrical housing, the overlap of the sleeve member with the distal end of the cylindrical member defining the chamber whereby slidable movement of the sleeve member with respect to the cylindrical member adjusts the length of the chamber to vary the size of the illumination spot at the disease site.

14. Apparatus as claimed in claim 13 in which the sleeve member is formed with a window for viewing inside the chamber to ensure proper positioning of the chamber over the disease site and a slidable cover to seal the window when the apparatus is in use.

15. Apparatus as claimed in claim 13 in which the free end of the sleeve member is cut at substantially 45 degrees to the longitudinal axis of the sleeve.

16. Apparatus as claimed in claim 1 wherein the apparatus further comprises a comparison spectrum able to distinguish spider angioma from each of actinic keratosis, seborrheic keratosis, basal cell carcinoma and compound nevus, wherein the spectrum indicates that if the fluorescence intensity is lower than normal and the reflectance ratio spectrum comprises a saw-tooth shape with a minimum at about 600 nm. then the disease is slider angioma, and the display indicates the presence or absence at the skin disease site of actinic keratosis, seborrheic keratosis, basal cell carcinoma, compound nevus or spider angioma.

17. Apparatus as claimed in claim 1 wherein the apparatus further comprises a comparison spectrum able to distinguish psoriasis from each of actinic keratosis, seborrheic keratosis, basal cell carcinoma and compound nevus, wherein the spectrum indicates that if the fluorescence spectral curve comprises an extra peak at about 635 nm. Then the disease is psoriasis, and the display indicates the presence or absence at the skin disease site of actinic keratosis, seborrheic keratosis, basal cell carcinoma, compound nevus or psoriasis.

18. Apparatus as claimed in claim 1 wherein the apparatus further comprises a comparison spectrum is able to distinguish squamous cell carcinoma from each of actinic keratosis, seborrheic keratosis, basal cell carcinoma and compound nevus, wherein the spectrum indicates that if the fluorescence intensity is lower than normal in some areas within the lesion and higher than normal in other areas within the lesion, then the disease is squamous cell carcinoma, and the display indicates the presence or absence at the skin disease site of actinic keratosis, seborrheic keratosis, basal cell carcinoma, compound nevus or squamous cell carcinoma.

19. Apparatus as claimed in claim 1 wherein the comparison spectra are stored in a computer.

20. An apparatus as claimed in claim 1 wherein the fluorescence is autofluorescence.

21. A method for diagnosis of a disease selected from the group consisting of actinic keratosis, seborrheic keratosis, basal cell carcinoma, compound nevus and spider angioma at a skin disease site using spectral analysis comprising the steps of:

illuminating the disease site with a light source to generate fluorescence and reflectance light at the disease site;
   collecting the generated fluorescence and reflectance light;
   conducting a spectral analysis of the collected light using a spectrometer;
   determining spectral measurements of the fluorescence light and the reflectance light;
   examining the spectral measurements together to make a diagnosis of the disease site, wherein the step of examining comprises comparing the spectral measurements with known spectral measurements and wherein if the reflectance curve slope is similar to normal and the fluorescence intensity is higher than normal, then determining that the disease is actinic keratosis; if the reflectance curve slope is similar to normal and the fluorescence intensity is lower than normal, then determining that the disease is basal cell carcinoma; if the reflectance curve slope is larger than normal and the fluorescence intensity is higher than normal, then determining that the disease is seborrheic keratosis; and, if the reflectance curve slope is larger than normal and the fluorescence intensity is lower than normal, then determining that the disease is compound nevus; and,
   displaying the diagnosis.

22. A method as claimed in claim 21 in which the steps of illuminating the disease site and collecting generated light involves sequentially illuminating the site with white light and collecting reflectance light and then illuminating the site with excitation light and collecting fluorescence light or vice versa.

23. A method as claimed in claim 22 including filtering the collected fluorescence light to filter out the excitation light.

24. A method as claimed in claim 21 in which a spectrometer card mounted in a personal computer is used to conduct a spectral analysis of the generated fluorescence and reflected light and display spectral measurements.

25. A method as claimed in claim 21 in which the step of collecting the generated fluorescence and reflectance light involves collecting light from the disease site and the surrounding normal skin.

26. A method as claimed in claim 25 in which the step of examining the spectral measurements involves comparing the disease site spectrum to the spectrum of the surrounding normal skin.

27. A method as claimed in claim 26 including the step of generating a ratio spectrum by dividing the disease site spectrum by the spectrum of the adjacent normal skin.

28. A method as claimed in claim 21 wherein, in the step of examining, if the fluorescence intensity is lower than normal and the reflectance ratio spectrum comprises a saw-tooth shape with a minimum at about 600 nm, then determining that the disease is spider angioma.

29. A method as claimed in claim 21 wherein, in the step of examining, if the fluorescence spectral curve comprises an extra peak at about 635 nm, then determining that the disease is psoriasis.

30. A method as claimed in claim 21 wherein, in the step of examining, if the fluorescence intensity is lower than normal in some areas within the lesion and higher than normal in other areas within the lesion, then determining that the disease is squamous cell carcinoma.

31. A method as claimed in claim 21 wherein the fluorescence is autofluorescence.

32. A combination able to diagnose a disease selected from the group consisting of actinic keratosis, seborrheic keratosis, basal cell carcinoma and compound nevus at a skin disease site using spectral analysis comprising:

a light source for generating light to illuminate the disease site;
   an optical probe optically connected to the light source to expose the disease site to light to generate fluorescence and reflectance light;
   a spectral analyzer optically connected to the optical probe for generating and displaying spectral measurements of the fluorescence light and the reflectance light to assist the user in diagnosing the disease site;
   a plurality of comparison spectra corresponding to, and able to distinguish between, each of actinic keratosis, seborrheic keratosis, basal cell carcinoma and compound nevus, wherein the spectra indicate that if the reflectance curve slope is similar to normal and the fluorescence intensity is higher than normal, then the disease is actinic keratosis; if the reflectance curve slope is similar to normal and the fluorescence intensity is lower than normal, then the disease is basal cell carcinoma; if the reflectance curve slope is larger than normal and the fluorescence intensity is higher than normal, then the disease is seborrheic keratosis; and, if the reflectance curve slope is larger than normal and the fluorescence intensity is lower than normal, then the disease is compound nevus; and
   a display indicating the presence or absence at the skin disease site, of actinic keratosis, seborrheic keratosis, basal cell carcinoma or compound nevus at the skin disease site.

33. A combination as claimed in claim 32 wherein the combination further comprises a comparison spectrum able to distinguish psoriasis from each of actinic keratosis, seborrheic keratosis, basal cell carcinoma and compound nevus, wherein the spectrum indicates that if the fluorescence spectral curve comprises an extra peak at about 635 nm, then the disease is psoriasis, and the display indicates the presence or absence at the skin disease site of actinic keratosis, basal cell carcinoma, compound nevus or psoriasis.

34. A combination as claimed in claim 33 wherein the comparison spectra are stored in a computer.

35. A combination as claimed in claim 32 wherein the combination further comprises a comparison spectrum able to distinguish squamous cell carcinoma from each of actinic keratosis, seborrheic keratosis, basal cell carcinoma and compound nevus wherein the spectrum indicates that if the fluorescence intensity is lower than normal in some areas within the lesion and higher than normal in other areas within the lesion, then the disease is squamous cell carcinoma, and the display indicates the presence or absence at the skin disease site of actinic keratosis, seborrheic keratosis, basal cell carcinoma, compound nevus or squamous cell carcinoma.

36. A combination as claimed in claim 35 wherein the comparison spectra are stored in a computer.

37. A combination as claimed in claim 32 wherein the comparison spectra are stored in a computer.

38. A combination as claimed in claim 32 wherein the fluorescence is autofluorescence.

39. A combination as claimed in 32 wherein the apparatus further comprises a comparison spectrum able to distinguish spider angioma from each of actinic keratosis, seborrheic keratosis, basal cell carcinoma and compound nevus, wherein the spectrum indicates that if the fluorescence intensity is lower than normal and the reflectance ratio spectrum comprises a saw-tooth shape with a minimum at about 600 nm, then the disease is spider angioma, and the display indicates the presence or absence at the skin disease site of actinic keratosis, seborrheic keratosis, basal cell carcinoma, compound nevus or spider angioma.

* * * * *

UNITED STATES PATENT AND TRADEMARK OFFICE
CERTIFICATE OF CORRECTION

PATENT NO. : 6,008,889
DATED : Dec. 28, 1999
INVENTOR(S) : Haishan Zeng, et al.

It is certified that error appears in the above-identified patent and that said Letters Patent is hereby corrected as shown below:

Column 8, line 62, claim 18, after "spectrum", delete "is".

Signed and Sealed this

Twenty-seventh Day of March, 2001

Attest:

NICHOLAS P. GODICI

Attesting Officer     Acting Director of the United States Patent and Trademark Office